United States Patent [19]

Akiyama

[11] Patent Number: 4,988,184
[45] Date of Patent: Jan. 29, 1991

[54] OPHTHALMIC DISEASE DETECTION APPARATUS

[75] Inventor: Koichi Akiyama, Tokyo, Japan
[73] Assignee: Kowa Company Ltd., Japan
[21] Appl. No.: 206,518
[22] Filed: Jun. 14, 1988
[30] Foreign Application Priority Data Jun. 18, 1987 [JP] Japan .................................. 62-150118

[51] Int. Cl.⁵ ............................................... A61B 3/10
[52] U.S. Cl. .................................. 351/221; 351/205; 351/214
[58] Field of Search ....................... 351/205, 214, 221; 606/5, 6

[56] References Cited
FOREIGN PATENT DOCUMENTS 225072  6/1987  European Pat. Off. ............ 351/221

Primary Examiner—Rodney B. Bovernick
Attorney, Agent, or Firm—Bruce L. Adams; Van C. Wilks

[57] ABSTRACT

An apparatus for examining for the presence of absence of opthalmic diseases in a patient's eye comprises a laser beam projector for projecting a laser beam at a selected spot in the patient's eye, an optical element disposed to receive light scattered by protein in the patient's eye, and a photoelectrical converter for photoelectrically converting the scattered light into an electrical signal. The laser beam projector and the optical element are arranged so that their optical axes cross substantially at right angles with each other. The optical element divides the scattered light into two parts, one part being directed to the photoelectrical converter and the other part being directed to observation equipment to enable an observer to view the selected spot in the patient's eye. The optical element is arranged so that the optical axis of the scattered light directed towards the photoelectrical converter lies in a common plane that includes both the optical axis of the laser beam projector and the optical axis of the scattered light received by the optical element.

13 Claims, 3 Drawing Sheets

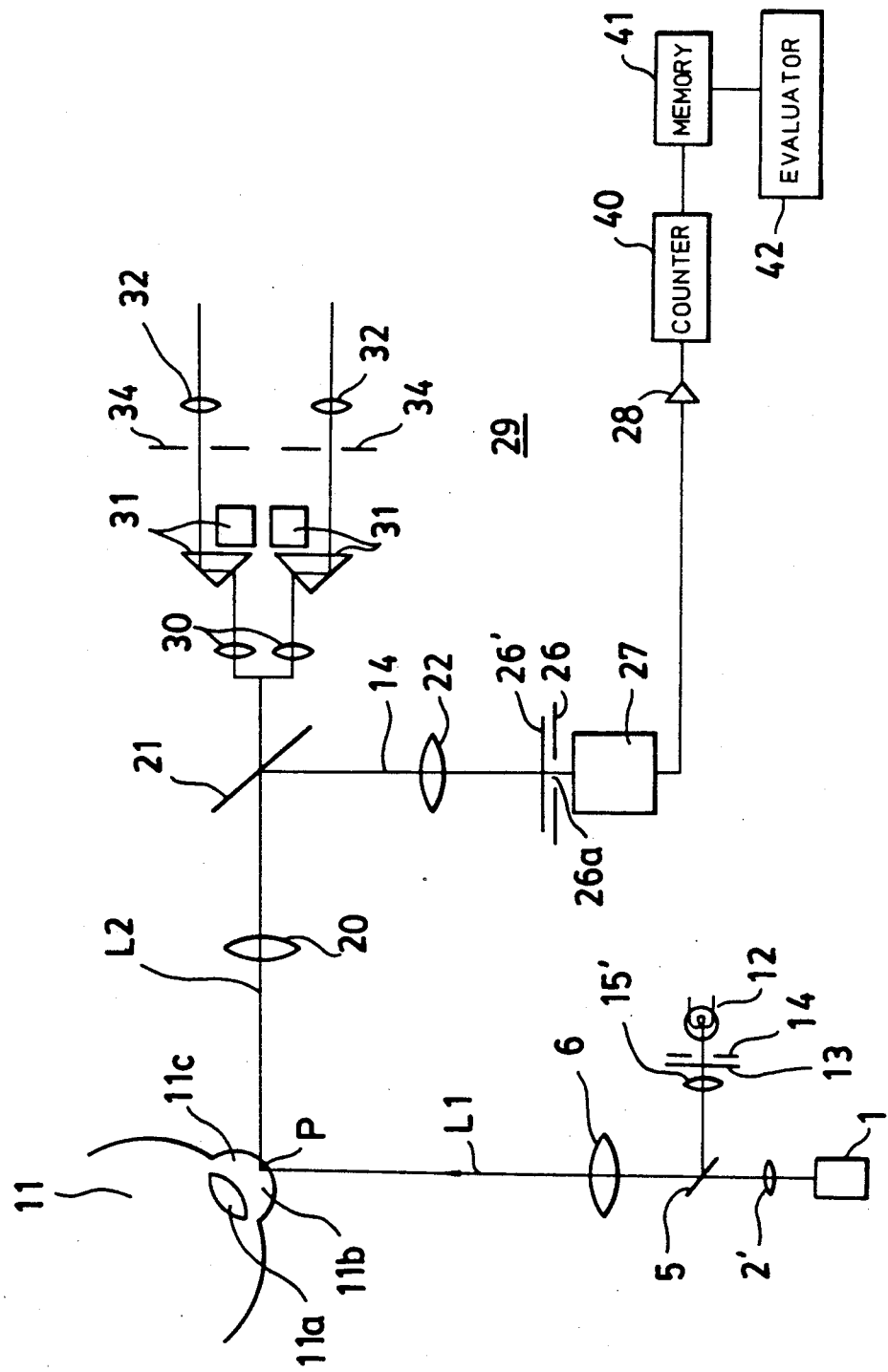

OPHTHALMIC DISEASE DETECTION APPARATUS

BACKGROUND OF THE INVENTION

1. Field of the Invention

This invention relates to an apparatus for examining for the presence or absence of ophthalmic diseases in a patient's eye, and more particularly to an apparatus for detecting ophthalmic diseases in which laser light is radiated via an optical system at one spot in the camera oculi of the patient's eye, particularly in the anterior chamber thereof, and the laser light scattered therefrom is analyzed to measure the protein concentration for ophthalmic disease detection in the camera oculi.

2. Description of the Prior Art

The camera oculi is comprised of the camera oculi anterior (anterior chamber) and the camera oculi posterior (posterior chamber). The camera oculi anterior is defined by a space surrounded by the rear surface of the cornea, a part of the ciliary body, the iris, and the front surface of the crystalline lens, while the camera oculi posterior is defined by a space surrounded by the rear surface of the iris, the inner surface of the ciliary body, and the front surface of the crystalline lens. The camera oculi is filled with transparent humor aqueous, which has chemical and physical characteristics that are different from those of lymphatic liquid and has a close relation with the metabolism of the cornea or crystalline lens. The humor aqueous contains proteins the increase of which causes turbidity in the camera oculi when it becomes inflamed.

In this respect, the measurement of protein concentration in the camera oculi of the patient's eye is of great importance in determining whether the camera oculi is inflamed, that is, whether a blood-aqueous barrier functions normally or not.

To measure the protein concentration in the camera oculi, a slit lamp microscope is very often used to determine the turbidity by grading via the naked eye. This is, however, disadvantageous because the judgment depends upon the person who performs the measurement.

On the other hand, a photographic measuring method has been developed to make a quantitative measurement of the protein concentration. This method is, however, highly complicated to analyze, and is thus very difficult to apply in a clinical examination.

To overcome this problem, an apparatus for detecting ophthalmic diseases has been proposed which includes means for focusing a laser beam at a selected spot in the camera oculi of an eye. In the apparatus, the light scattered from the eye is photoelectrically detected and converted into an electrical signal which is subsequently used to determine the protein concentration essential to ophthalmic disease detection in the camera oculi of the patient's eye. See, for example, Japanese Patent Laying-open No. 120834/87.

Such use of a laser beam to focus on a selected spot in the camera oculi of an eye for ophthalmic measurement by detecting light scattered from the eye conventionally has been accompanied by such problems as an increased intensity of the laser beam imposing major discomfort on the patient as well as a high risk. If, in order to avoid this, a small-output laser light source is employed, the intensity of the laser beam impinging on the camera oculi is reduced, and as a consequence it is necessary to raise the sensitivity of the light detection system, raising the cost of the overall apparatus.

SUMMARY OF THE INVENTION

An object of the present invention is therefore to provide an ophthalmic disease detection apparatus which, with respect to the patient, imposes as little discomfort as possible and involves little risk, in addition to which the output of the laser light source can be small, enabling the overall apparatus to be made compact in size.

An apparatus for detecting ophthalmic diseases in a patient's eye according to the present invention comprises a light transmitting means which comprises a laser source for producing a laser beam, a laser beam projector for projecting the laser beam along a first optical axis, means for focusing the laser beam at a selected spot in the patient's eye, light receiving means including visual observing means or observation equipment for observing light scattered from the spot in the patient's eye and a photoelectric converting means photoelectrical converter for photoelectrically converting the scattered light into an electrical signal, and means for processing the electrical signal to evaluate the ophthalmic diseases in the patent's eye. The laser beam projector and light receiving means are arranged so that their optical axes cross substantially at right angles with each other An optical element or light guiding means lying along a second optical axis is further provided in the light receiving means to divide the scattered light on to the photoelectrical converter and observation equipment. The optical element is arranged so that the optical axis of the scattered light directed towards the photoelectrical converter lies in a plane that includes the optical axes of the laser beam projector and the light receiving means.

Because in accordance with the said arrangement the laser beam projector and the light receiving means are arranged at a set angle or 90 degrees to each other, light scattered laterally is received from an angle of 90 degrees. Therefore, the scattered laser light is formed almost entirely of polarized (S-polarized) components perpendicular to the plane of incidence, that is, a plane that includes the incident laser beam and the reflected beam. An optical element such as a semi-transparent mirror or a beam splitter for guiding the scattered laser light along a third optical axis to a photoelectric converter is positioned so that the optical axis of the laser light scattered towards the photoelectric converter is in a plane that includes the optical axes of the laser beam projector and laser light receiving means, so that laser light scattered from the camera oculi impinges on the said semi-transparent mirror or beam splitter as S-polarized light, therefore facilitating the reflection thereof, S-polarized light generally being readily reflected. Thus, it becomes possible to efficiently guide the scattered light to the photoelectric converter.

Thus, as in accordance with this invention, a semi-transparent mirror is disposed so that the optical axis of the laser light scattered towards the photoelectrical converter is positioned in a plane that includes the optical axes of the laser beam projector and the laser light receiving means, thereby enabling the scattered light to be guided efficiently to the photoelectric converter, making it is possible to decrease the output of the projected laser beam by a corresponding amount. Not only does this reduce the amount of discomfort on the patient by enabling the laser light source to be made smaller, but it also makes it possible to reduce the cost of the overall apparatus.

BRIEF DESCRIPTION OF THE DRAWINGS

The objects and features of the present invention will become more apparent from a consideration of the following detailed description taken in conjunction with the accompanying drawings in which:

FIG. 2 (B) is a drawing showing the arrangement of the optical system of the apparatus viewed along a perpendicular cross-section.

DETAILED DESCRIPTION OF THE PREFERRED EMBODIMENTS

The invention will now be described in detail with reference to the drawings.

Figure 1:
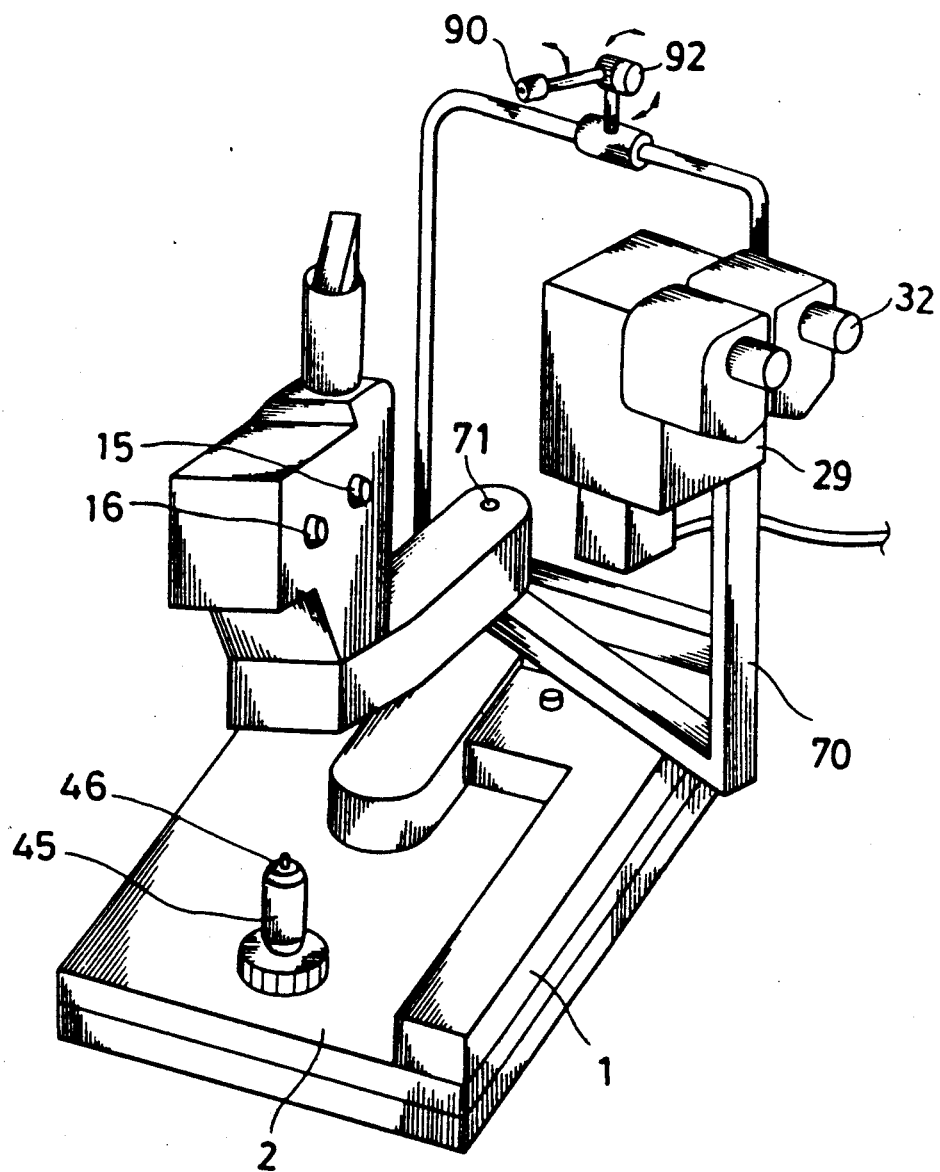
FIG. 1 is a general perspective view of an apparatus according to the present invention.
Figure 2B:
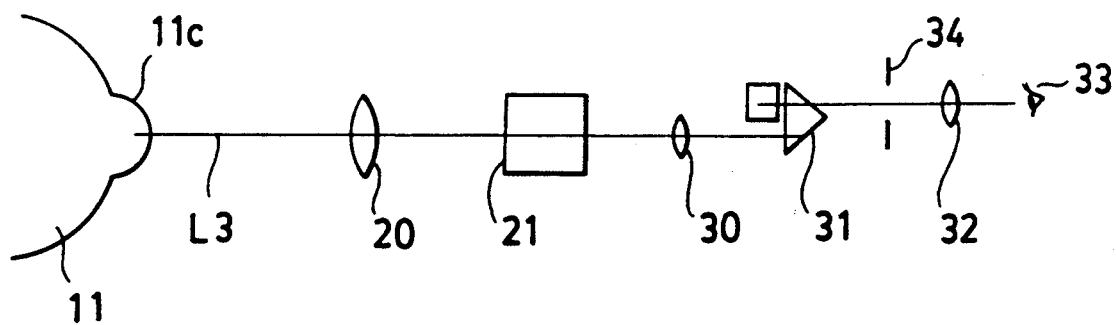
FIG. 2 (A) is a drawing showing the arrangement of the optical system of the apparatus viewed along a horizontal cross-section.

In FIGS. 1 and 2 which show an arrangement of the ophthalmic disease detection apparatus according to the present invention, reference numeral 1 denotes a laser light source, such as, for example, a helium-neon or argon laser source. The laser light source 1 is disposed on a stand 2. Light from the laser light source 1 is arranged to pass along the optical axis L1 of first optical axis of a laser beam projector, through a lens 2', a beam splitter 5 and a condenser lens 6 to converge on the eye under examination at a spot P in the anterior aqueous humor 11c on the inner side of the cornea 11b and to the front of the crystalline lens 11a.

The laser beam projector is provided with a slit light source 12. As shown in FIG. 2 (A), light from the slit light source 12 passes via a slit 14, a shutter 13 and a lens 15' to the beam splitter 5 and passes along the optical axis L1 to form a slit image in the region of the aqueous humor 11c. Because the light from the laser light source converges to form a spot, this slit image can be used to illuminate the surrounding area thereof to facilitate confirmation of the position of the spot of converged light.

The width and length of the slit 14 can be adjusted by an adjusting knob 15 and a switching knob 16, respectively, which are shown in FIG. 1.

The laser light scattered from the measuring spot P in the aqueous humor 11c advances along an optical axis L2 or second optical axis to an objective lens 20 and is split by a semitransparent mirror or a beam splitter 21. One part of the light passes along a third optical axis through a lens 22, a shutter 26' and a mask 26 provided with a slit 26a and impinges on a photoelectric converter 27 comprised of, for example, a photomultiplier. The other part of the scattered light split by the beam splitter 21 passes along a fourth optical axis via a lens 30, a prism 31 and a field-of-vision stop 34 to an eyepiece 32 by means of which an examiner 33 carries out observations. With this embodiment the beam splitter 21 is positioned so that, as shown in FIG. 2 (B), the optical axis of the scattered laser light that goes to the photoelectric converter 27 is in a plane L3 that includes the optical axes L1 and L2 of the laser beam projector and the light receiving means.

The output from the photoelectric converter 27 is passed through an amplifier 28 and is input to a counter or counting means 40 and the intensity of the scattered light detected by the photoelectric converter is counted as a number of pulses per unit time. The output of the counter, i.e., the number of samplings or the total pulse count, is stored in a memory or memory means 41 allocated for each unit time. The data stored in the memory 41 is processed by an evaluating device 42 which computes the cell count and the concentration of protein in the anterior chamber.

As shown in FIG. 1, the light receiving means 29 is affixed to a support 70. The support 70 and the laser beam projector are provided so as to be rotatable, with respect to each other, about a shaft 71 so as to allow the angle between the optical axes of the laser beam projector and the light receiving means to be adjusted to an optimum setting. As shown in FIG. 2 (A), in this embodiment, the optical axis L1 of the laser beam projector is arranged at an angle of approximately 90 degrees to the optical axis L2 of the light receiving means, so the light receiving means receives the light laterally, at this angle of 90 degrees.

Also in accordance with this embodiment, an eye fixation light 90 constituted of a light-emitting diode or the like is provided at a position that permits fixation of the patient's eye by the examiner. The eye fixation light 90 can be turned in the direction indicated by the arrow by means of a link mechanism 92 to enable it to be adjusted to an optimum position with respect to the examiner. Provided on the base 2 is an input means such as a joystick 45 equipped with a push-button 46, and this can be operated to insert into, or retract from, the optical system such optical elements as shutters and filters.

The operation of the apparatus arranged thus will now be described. In conducting the measurement, the slit light source 12 is activated and an image of the slit 14 is formed on a portion of the anterior aqueous humor 11c that includes the measuring point P. Following this, light from the laser light source 1 is converged on the measuring point P by means of the laser light projector system.

Figure 3:
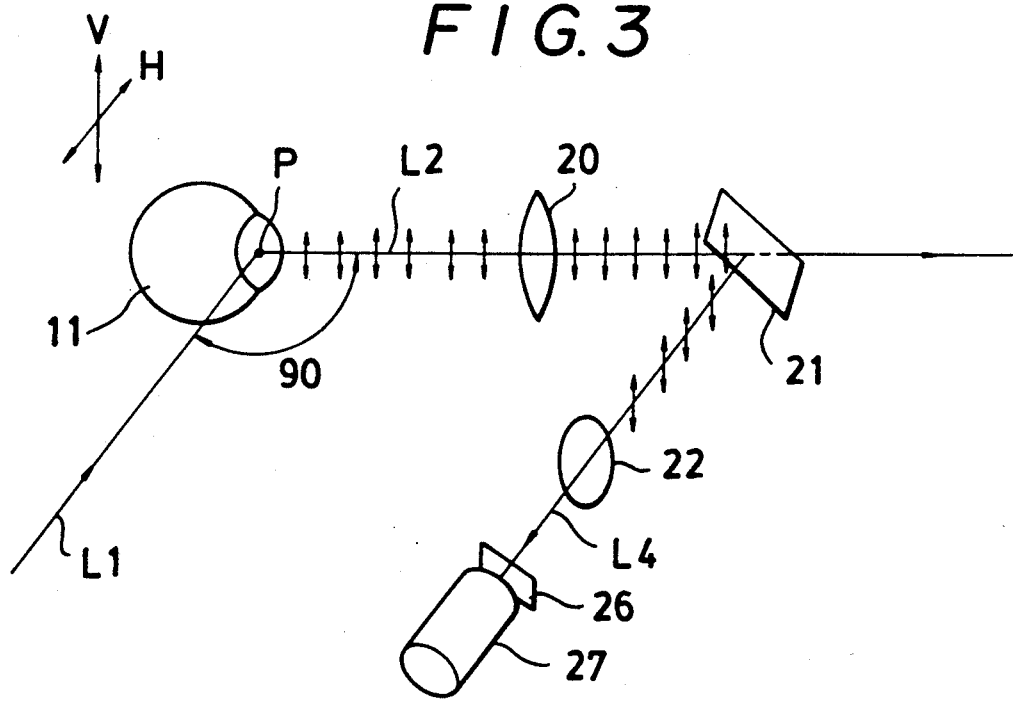
FIG. 3 is an explanatory drawing illustrating the effect of the apparatus of the invention.

A portion of the light scattered from the measuring point P is simultaneously directed by the beam splitter 21 to the examiner 33 for observation and through a lens 22, shutter 26' and mask 26 to impinge on the photoelectric converter 27. Because in accordance with the present embodiment, as described above, the optical axis L1 of the laser beam projector and the optical axis L2 of the light receiving means are arranged at substantially 90 degrees to each other, the photoelectric converter 27 receives light scattered laterally from an angle of 90 degrees. In this case, as illustrated in FIG. 3, almost all the components of the light scattered at 90 degrees are polarized (S-polarized) components perpendicular to the plane that includes the optical axes L1 and L2 (in the drawing this polarized component portion is indicated by the vertical double-headed arrows). The beam splitter 21 is positioned so that the S-polarized component impinges thereon, i.e., so that an optical axis L4 of the scattered laser light is in a plane that includes the optical axes L1 and L2, which enables the scattered light to be efficiently guided to the photoelectric converter 27. The photoelectric converter 27 detects the intensity of the light and converts this into a corresponding series of pulses which are counted by a counter 40 as numbers of pulses per unit time and the count values are stored in the memory 41 allocated for each unit time, and the evaluating device 42 processes the data contained in the memory 41 to evaluate the protein concentration and blood cell count.

Since the transmittivity (also reflectivity) of the beam splitter 21 can be set as required, the sensitivity can be raised simply by increasing the amount of light directed at the photoelectric converter. However, the light for observation purposes will be reduced by a corresponding amount, making observation more difficult, and this, in turn, can make positional alignment more difficult. With this arrangement according to the first embodiment of the invention, the amount of light for observation purposes can be maintained unchanged, with only the quantity of scattered laser light (signal component) being increased.

Figure 4:
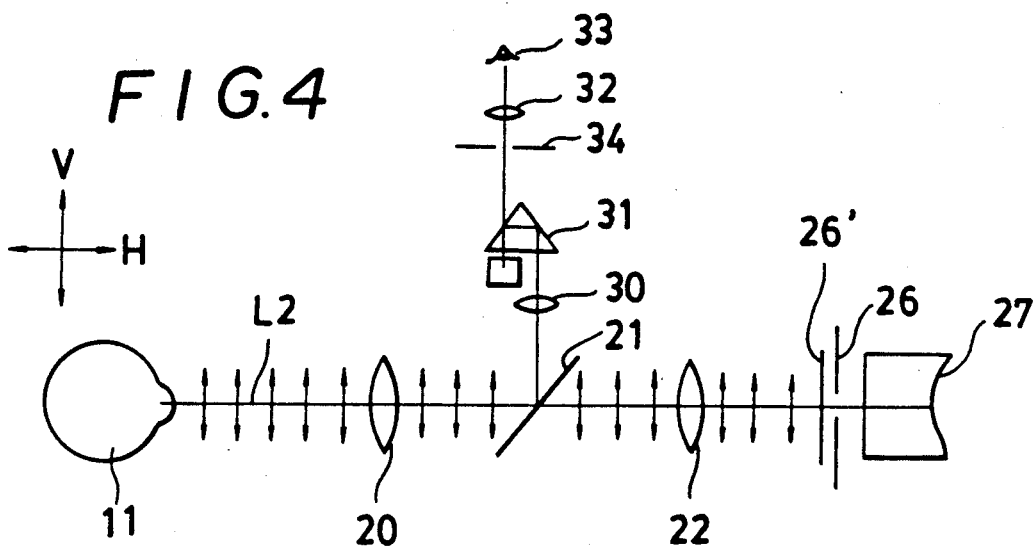
FIG. 4 is a drawing showing the arrangement of the optical system of another embodiment of the apparatus.

FIG. 4 shows another embodiment of the present invention. In this embodiment, the relationship between the observation system and the signal light receiving means has been reversed. With this arrangement, the scattered light impinges on the semitransparent mirror (or beam splitter) as P polarized light, facilitating the transmission there of, and then impinges on the photoelectric converter 27. With this arrangement the process of observation of the scattered light by the examiner 33 is carried out from above.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

I claim:

1. An apparatus for examining for the presence or absence of ophthalmic diseases in a patient's eye comprising:
   a laser source for producing a laser beam;
   a laser beam projector for projecting said laser beam;
   means for focusing said laser beam at a selected spot in the patient's eye;
   light receiving means including observation equipment for observing light scattered from said spot in the patient's eye and a photoelectrical converter for photoelectrically converting the scattered light in an electrical signal, said laser beam projector and light receiving means being arranged so that their optical axes cross substantially at right angles to produce laterally scattered light which is formed almost entirely of polarized components perpendicular to the plane of incidence; and
   means for processing said electrical signal to determine the presence or absence of ophthalmic diseases in the patient's eye;
   wherein an optical element is provided in said light receiving means to divide the scattered light into said photoelectrical converter and said observation equipment, said optical element being arranged so that the optical axis of said scattered light directed towards said photoelectrical converter lies in a plane that includes the optical axes of said laser beam projector and said light receiving means so as to guide the polarized scattered light without changing the polarization thereof to the photoelectrical converter.

2. An apparatus as set forth in claim 1; wherein said optical element is a semi-transparent mirror or beam splitter.

3. An apparatus for measuring protein concentration in a patient's eye comprising:
   light transmitting means for transmitting a beam of laser light along a first optical axis onto a spot in a patient's eye whereby the laser beam is scattered by protein in the patient's eye;
   light guiding means disposed along a second optical axis for receiving scattered light polarized in a given direction and for guiding the scattered and polarized light along a third optical axis without changing the polarization thereof, said second optical axis being at a set angle relative to said first optical axis and said third optical axis lying in a common plane with said first and second optical axes;
   photoelectric converting means disposed along the third optical axis for receiving the scattered and polarized light and for converting and processing means to determine the protein concentration in the patient's eye.

4. An apparatus for measuring protein concentration in a patient's eye according to claim 3; wherein said light guiding means includes means for guiding the scattered and polarized light along a fourth optical axis; and
   visual observing means disposed along the fourth optical axis for enabling visual observation of the spot in the patient's eye.

5. An apparatus for measuring protein concentration in a patient's eye according to claim 3; wherein said light guiding means comprises an optical element.

6. An apparatus for measuring protein concentration in a patient's eye according to claim 5; wherein said optical element comprises a beam splitter.

7. An apparatus for measuring protein concentration in a patient's eye according to claim 5; wherein said optical element comprises a semi-transparent mirror.

8. An apparatus for measuring protein concentration in a patient's eye according to claim 3; wherein said photoelectric converting means includes means for producing electrical signals comprised of pulses.

9. An apparatus for measuring protein concentration in a patient's eye according to claim 3; wherein said photoelectric converting means comprises a photomultiplier.

10. An apparatus for measuring protein concentration in a patient's eye according to claim 3; wherein said light guiding means is disposed to receive S-polarized, scattered light.

11. An apparatus for measuring protein concentration in a patient's eye according to claim 3; wherein said light guiding means is disposed to receive P-polarized, scattered light.

12. An apparatus for measuring protein concentration in a patient's eye according to claim 3; wherein said light guiding means is disposed on said second optical axis, said second optical axis being at a set angle of 90 degrees to said first optical axis.

13. An apparatus for measuring protein concentration in a patient's eye according to claim 3; wherein said means for processing comprises counting means for counting the number of electrical signals from said photoelectric converting means and outputting a corresponding count, memory means for storing the count and means for evaluating the count and determining therefrom the protein concentration.

* * * * *